United States Patent
Dirkzwager et al.

(10) Patent No.: US 7,105,706 B2
(45) Date of Patent: Sep. 12, 2006

(54) PROCESS FOR THE PREPARATION OF AN ALKOXYLATED ALCOHOL COMPOSITION

(75) Inventors: Hendrik Dirkzwager, Amsterdam (NL); Laurent Alain Fenouil, East Twickenham (GB); Rendert Jan Wiersma, Amsterdam (NL)

(73) Assignee: Shell Oil Company, Houston, TX (US)

( * ) Notice: Subject to any disclaimer, the term of this patent is extended or adjusted under 35 U.S.C. 154(b) by 41 days.

(21) Appl. No.: 11/008,047

(22) Filed: Dec. 9, 2004

(65) Prior Publication Data

US 2005/0192363 A1 Sep. 1, 2005

Related U.S. Application Data

(60) Provisional application No. 60/528,693, filed on Dec. 11, 2003.

(51) Int. Cl.
*C07C 43/11* (2006.01)
*C07C 27/00* (2006.01)
*C11D 3/00* (2006.01)

(52) U.S. Cl. .......... 568/618; 518/700; 518/715; 510/524

(58) Field of Classification Search .......... 518/700, 518/715; 568/618; 510/524
See application file for complete search history.

(56) References Cited

U.S. PATENT DOCUMENTS

| | | | |
|---|---|---|---|
| 5,057,627 A | 10/1991 | Edwards | 568/618 |
| 5,907,067 A * | 5/1999 | Barnhorst et al. | 568/618 |
| 6,706,931 B1 | 3/2004 | Edwards | 568/671 |
| 6,740,683 B1 | 5/2004 | Price | 518/719 |
| 2003/0018086 A1 | 1/2003 | Price | 518/702 |

FOREIGN PATENT DOCUMENTS

| | | |
|---|---|---|
| DE | 00/14045 | 3/2000 |
| EP | 345861 | 12/1989 |
| WO | 02/47817 | 6/2002 |
| WO | 2 483 470 | 11/2003 |

OTHER PUBLICATIONS

A.P. Steynberg, R.L. Espinoza, B. Jager, A.C. Vosloo, "High Temperature Fischer-Tropsch synthesis in commercial practice", Applied Catalysis A:General 186(1999), pp. 41-54.
Frohning et al in Falbe; Chemical Feedstocks from Coal; Chapter 8; Fischer-Tropsch Process, pp. 309-432, John Wiley & Sons, 1982.

* cited by examiner

*Primary Examiner*—J. Parsa
(74) *Attorney, Agent, or Firm*—Donald F. Haas

(57) ABSTRACT

Process for the preparation of an alkoxylated alcohol composition comprising one or more alkoxylated alcohols wherein the process comprises the steps of:
(a) reacting carbon monoxide with hydrogen under Fischer-Tropsch reaction conditions in the presence of a Fischer-Tropsch catalyst;
(b) separating from the product of step (a) at least one hydrocarbon fraction comprising paraffins having from 9 to 17 carbon atoms and olefins having from 9 to 17 carbon atoms, the hydrocarbon fraction additionally comprising at least a portion of alcohols;
(c) contacting one or more of the hydrocarbon fractions obtained in step (b) with an alkylene oxide; and
(d) recovering an alkoxylated alcohol composition from the reaction product of step (c).

17 Claims, No Drawings

PROCESS FOR THE PREPARATION OF AN ALKOXYLATED ALCOHOL COMPOSITION

REFERENCE TO PRIOR APPLICATION

This application claims the benefit of U.S. provisional application Ser. No. 60/528,693, filed Dec. 11, 2003, the entire disclosure of which is hereby incorporated by reference.

FIELD OF THE INVENTION

The present invention relates to a process for the preparation of an alkoxylated alcohol composition, more specifically to a process for preparing an alkoxylated alcohol composition by direct alkoxylation of the alcohols present in a Fischer-Tropsch reaction product.

BACKGROUND OF THE INVENTION

A large variety of products useful, for instance, as nonionic surfactants, wetting and emulsifying agents, solvents and chemical intermediates are prepared by the addition reaction (alkoxylation reaction) of alkylene oxides (epoxides) with organic compounds having one or more active hydrogen atoms. For example, particular mention may be made of the alcohol ethoxylates prepared by the reaction of ethylene oxide with aliphatic alcohols of 6 to 30 carbon atoms. Such ethoxylates, and to a lesser extent corresponding propoxylates and compounds containing mixed oxyethylene and oxypropylene groups, are widely employed as nonionic detergent components in cleaning and personal care formulations.

An illustration of the preparation of an alkanol ethoxylate (represented by formula III below) by addition of a number (n) of ethylene oxide molecules (formula II) to a single alkanol molecule (formula I) is presented by the equation:

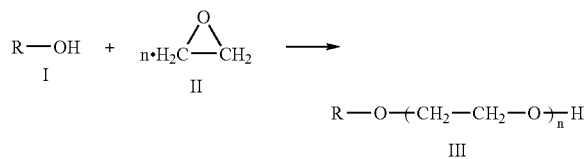

One typical method of preparing such alkoxylated alcohols is by hydroformylating an olefin into an oxo-alcohol, followed by alkoxylation of the resulting alcohol by reaction with a suitable alkylene oxide such as ethylene oxide or propylene oxide.

Typically the olefin to be hydroformylated is obtained by the oligomerization of ethylene, for example as is used in the Shell Higher Olefin Process (SHOP).

Hydroformylation is typically conducted in the presence of a homogeneous catalyst which is based on a source of a transition metal, typically a metal of Group 8 (iron, ruthenium or osmium), 9 (cobalt, rhodium or iridium) or 10 (nickel, palladium or platinum) of the Periodic Table of Elements. In their catalytically active form these metals may be used with carbonyl ligands, but they can also be used as a complex with other ligands, suitably phosphorus-containing ligands. Such catalysts are commonly referred to as phosphine and/or phosphite-modified hydroformylation catalysts.

The first stage of the hydroformylation reaction is formation of an oxo-aldehyde. This is followed by a secondary reaction involving the hydrogenation of the oxo-aldehyde into the corresponding oxo-alcohol. The secondary reaction may occur simultaneously with the actual hydroformylation reaction, depending on the type of catalyst used. Some of the homogeneous hydroformylation catalysts are sufficiently active to hydrogenate the in-situ formed oxo-aldehyde into the desired oxo-alcohol. Sometimes, however, a separate hydrofinishing step is applied in order to improve the quality of the final oxo-alcohol product in terms of its aldehyde content.

Once the oxo-alcohols have been alkoxylated, they may be used as nonionic surfactants in a wide variety of products, such as, for example, detergent compositions, lubricants and personal care compositions. Especially useful for this purpose are ethoxylated and/or propoxylated alcohols which contain from 9 to 17 carbon atoms in the carbon backbone, excluding the carbon atoms in ethoxy/propoxy groups.

As can be seen from the above discussion, current commercial processes for producing ethoxylated alcohols involve multi-step processes, for example involving the following steps (1)–(3): (1) oligomerization of ethylene to produce an olefin, (2) hydroformylation of the olefin to produce an alcohol, and (3) alkoxylation of the alcohol to produce an alkoxylated alcohol. Further, currently used processes for producing alkoxylated alcohols are based on ethylene feedstocks, which tend to be relatively expensive.

In view of the high demand in the detergents industry for nonionic alkoxylated alcohol surfactants, it would be desirable to provide a less complex process for preparing alkoxylated alcohols. At the same time, it would be desirable to make use of feedstocks which are cheaper than ethylene. In particular, it would be desirable to make use of feedstocks derived from the "Fischer-Tropsch" hydrocarbon synthesis which involves the reaction of carbon monoxide and hydrogen ("synthesis gas") to produce hydrocarbons. The synthesis gas used in the Fischer-Tropsch hydrocarbon synthesis is derived from cheap, abundantly available natural gas or coal.

In addition to hydrocarbons such as paraffins and olefins, feedstocks derived from the Fischer-Tropsch process typically also contain a certain amount of oxygenate components such as alcohols and aldehydes. The amount of alcohols present in the Fischer-Tropsch stream varies depending on the type of catalyst used, although it may be relatively low compared with the amount of hydrocarbons (e.g. paraffins). It has now surprisingly been found by the present inventors that despite the relatively low levels of alcohols present in feedstocks derived from the Fischer-Tropsch synthesis, these alcohols can be ethoxylated directly. This leads to a process for preparing ethoxylated alcohols which comprises fewer steps than current commercial processes. In addition, the process of the present invention enables the use of Fischer-Tropsch derived feedstocks that tend to be cheap relative to ethylene feedstocks and contain very low levels of sulphur and/or nitrogen contaminants.

SUMMARY OF THE INVENTION

Accordingly, the present invention provides a process for the preparation of an alkoxylated alcohol composition comprising one or more alkoxylated alcohols wherein the process comprises the steps of:

(a) reacting carbon monoxide with hydrogen under Fischer-Tropsch reaction conditions in the presence of a Fischer-Tropsch catalyst;

(b) separating from the product of step (a) at least one hydrocarbon fraction comprising a mixture of paraffins having from 9 to 17 carbon atoms and olefins having from 9 to 17 carbon atoms, the hydrocarbon fraction additionally comprising at least a portion of alcohols;

(c) contacting one or more of the hydrocarbon fractions obtained in step (b) with an alkylene oxide; and (d) recovering an alkoxylated alcohol composition from the reaction product of step (c).

DETAILED DESCRIPTION OF THE INVENTION

In step (a) of the present process hydrocarbons are prepared by reacting carbon monoxide and hydrogen under suitable conditions. In general, the preparation of hydrocarbons from a mixture of carbon monoxide and hydrogen at elevated temperature and pressure in the presence of a suitable catalyst is known as the Fischer-Tropsch hydrocarbon synthesis. Catalysts used in this hydrocarbon synthesis are normally referred to as Fischer-Tropsch catalysts and usually comprise one or more metals from Groups 8, 9 and 10 of the Periodic Table of Elements, optionally together with one or more promoters, and a carrier material. In particular, iron, nickel, cobalt and ruthenium are well known catalytically active metals for such catalysts and can be used in the present process.

The catalyst preferably also comprises a porous carrier material, in particular a refractory oxide carrier. Examples of suitable refractory oxide carriers include alumina, silica, titania, zirconia or mixtures thereof, such as silica-alumina or physical mixtures such as silica and titania. Particularly suitable carriers are those comprising titania, zirconia or mixtures thereof.

In one embodiment of the present invention the catalyst is a cobalt-based Fischer-Tropsch catalyst.

In the case of cobalt-based Fischer-Tropsch catalysts, titania carriers are preferred, in particular titania which has been prepared in the absence of sulphur-containing compounds. This carrier may further comprise up to about 50% by weight of another refractory oxide, typically silica or alumina. More preferably, the additional refractory oxide, if present, constitutes up to 20% by weight, even more preferably up to 10% by weight, of the carrier.

Typically, a cobalt-based Fischer-Tropsch catalyst comprises about 1–100 parts by weight of cobalt (calculated as element), preferably about 3–60 parts by weight and more preferably about 5–40 parts by weight, per 100 parts by weight of carrier. These amounts of cobalt refer to the total amount of cobalt in elemental form and can be determined by known elemental analysis techniques.

In addition to cobalt the catalyst may comprise one or more promoters known to those skilled in the art. Suitable promoters include manganese, zirconium, titanium, ruthenium, platinum, vanadium, palladium and/or rhenium. The amount of promoter, if present, is typically between about 0.1 and about 150 parts by weight (calculated as element), for example between about 0.25 and about 50, more suitably between about 0.5 and about 20 and even more suitably between about 0.5 and about 10, parts by weight per 100 parts by weight of carrier.

Typically, the cobalt-based Fischer-Tropsch catalyst does not contain alkali or alkaline earth metals, apart from possible impurities introduced with starting materials in the preparation process of the catalysts of the present invention. Typically, the atomic ratio of alkali or alkaline earth metals to cobalt metal is less than about 0.01, preferably less than about 0.005.

In another embodiment of the present invention the Fischer-Tropsch catalyst is an iron-based Fischer-Tropsch catalyst. An iron-based Fischer-Tropsch catalyst is preferred for use herein from the viewpoint of maximizing the level of alcohols in the Fischer-Tropsch reaction product. In particular, suitable iron-based Fischer-Tropsch catalysts include those disclosed in U.S. Pat. No. 6,740,683, which is herein incorporated by reference in its entirety. Alternative iron-based Fischer-Tropsch catalysts include those used in the so-called "Synthol" process. Details of catalysts used in the Synthol process can be found in Frohning et al in Falbe; Chemical Feedstocks from Coal; Chapter 8; Fischer-Tropsch Process, pages 309–432, John Wiley & Sons, 1982. In particular, page 396 discloses details of Synthol catalyst preparation.

In the case of cobalt-based Fischer-Tropsch catalysts, the Fischer-Tropsch process conditions applied in step (a) of the present process typically involve a temperature in the range from about 125 to about 350° C., preferably about 160 to about 275° C., more preferably from about 175 to about 250° C., even more preferably from about 190 to about 240° C., and especially from about 190 to about 235° C., and a pressure in the range from about 5 to about 150 bar abs. Step (a) of the present process may be operated at the pressures conventionally applied, i.e. up to about 80 bar abs., suitably up to about 65 bar abs., but also higher pressures can be applied.

In the case of cobalt-based Fischer-Tropsch catalysts, one preferred embodiment involves a pressure in step (a) of at least about 30 bar, preferably at least about 50 bar. A much preferred pressure range is about 50 to about 150 bar, even more preferably about 55 to about 140 bar. Operating temperatures at these pressures may be those normally applied, but preferred operating temperatures at these pressures are in the range of from about 150 to about 250° C., more preferably about 160 to about 230° C.

In the case of an iron-based Fischer-Tropsch catalyst, in particular those catalysts disclosed in U.S. Pat. No. 6,740,683, which is herein incorporated by reference in its entirety, the Fischer-Tropsch process conditions applied in step (a) of the present process are preferably those as disclosed in U.S. Pat. No. 6,740,683.

In the case of an iron-based Synthol-type catalyst, the Fischer-Tropsch process conditions applied in step (a) of the present process are those as used in the so-called Synthol process as disclosed in Frohning et al in Falbe; Chemical Feedstocks from Coal; Chapter 8; Fischer-Tropsch Process, pages 309–432, John Wiley & Sons, 1982 and A. P. Steynberg, R. L. Espinoza, B. Jager, A. C. Vosloo, "High Temperature Fischer-Tropsch synthesis in commercial practice", Applied Catalysis A:General 186 (1999), pages 41–54.

In a preferred embodiment of the present invention step (a) comprises reacting carbon monoxide with hydrogen at a temperature in the range of from about 125 to about 350° C. and a pressure in the range from about 5 to about 150 bar in the presence of a catalyst comprising cobalt on a carrier comprising titania.

In particularly preferred embodiments herein, the catalyst and process conditions in step (a) are selected such that the product obtained in step (a) comprises in the range of from about 2 to about 20% by weight of a C11 to C14 hydrocarbon fraction, which hydrocarbon fraction comprises at least about 2%, preferably at least about 10%, more preferably at least about 30%, by weight, of C9 to C12 mono-alcohols.

This could, for instance, be achieved by using a cobalt-based Fischer-Tropsch catalyst based on cobalt and titania at operating temperatures of about 175 to about 275° C. and operating pressures of from about 30 up to about 65 bar abs., or by using an iron-based Fischer-Tropsch catalyst such as those disclosed in U.S. Pat. No. 6,740,683, which is herein incorporated by reference in its entirety.

Hydrogen and carbon monoxide (synthesis gas) are typically fed to the reactor at a molar ratio in the range from about 0.5 to about 4, preferably from about 0.5 to about 3, more preferably from about 0.5 to about 2.5 and especially from about 1.0 to about 1.5. These molar ratios are preferred for the case of a fixed bed reactor.

The Fischer-Tropsch reaction step (a) may be conducted using a variety of reactor types and reaction regimes, for example a fixed bed regime, a slurry phase regime or an ebullating bed regime. It will be appreciated that the size of the catalyst particles may vary depending on the reaction regime they are intended for. It is within the normal skills of the skilled person to select the most appropriate catalyst particle size for a given reaction regime.

Further, it will be understood that the skilled person is capable to select the most appropriate conditions for a specific reactor configuration and reaction regime. For example, the preferred gas hourly space velocity may depend upon the type of reaction regime that is being applied. Thus, if it is desired to operate the hydrocarbon synthesis process with a fixed bed regime, preferably the gas hourly space velocity is chosen in the range from about 500 to about 2500 Nl/l/h. If it is desired to operate the hydrocarbon synthesis process with a slurry phase regime, preferably the gas hourly space velocity is chosen in the range from about 1500 to about 7500 Nl/l/h.

After carbon monoxide and hydrogen have reacted to produce a hydrocarbon product in step (a), this hydrocarbon product is separated in subsequent step (b) into one or more hydrocarbon fractions comprising at least about 2% by weight, preferably at least about 10% by weight, of alcohols. Preferably the separation in step (b) involves a distillation treatment. Conventional distillation techniques can be used. For example the separation step in step (b) could involve fractional distillation, but the separation step could also comprise a combination of distillation with another separation treatment, such as condensation and/or extraction.

As used herein, the term "hydrocarbon fraction" means a portion of the Fischer-Tropsch reaction product which boils within a certain temperature range. Said portion comprises a mixture of compounds synthesized in the Fischer-Tropsch reaction such as paraffins, olefins and alcohols. The compounds in a particular hydrocarbon fraction each have boiling points within the boiling point range for that hydrocarbon fraction.

The particular hydrocarbon fraction selected will depend on the desired end use of the alkoxylated alcohols. Particularly suitable for use herein are hydrocarbon fractions which comprise paraffins and olefins having from 9 to 17 carbon atoms.

Paraffins and olefins having the same number of carbon atoms, n, tend to have boiling points within about 5° C. or less of each other. Therefore hydrocarbon fractions can also be described in terms of the number of carbon atoms present in the paraffins and olefins contained therein. Hence a "C9" hydrocarbon fraction will generally comprise paraffins having 9 carbon atoms and olefins having 9 carbon atoms. Suitable hydrocarbon fractions herein may be designated as "C9", "C10", "C11", "C12", "C13", "C14", "C15", "C16", "C17" hydrocarbon fractions. Since alcohols having n carbon atoms tend to have higher boiling points than paraffins and olefins having n carbon atoms, a Cn hydrocarbon fraction will tend to comprise C(n-2) alcohols.

Other suitable hydrocarbon fractions may comprise a mixture of paraffins and olefins having a wider range of carbon atom numbers (and hence having a wider boiling point range). For example, other such hydrocarbon fractions suitable for use herein include the C8–C10, C11–C12, C13–C14 and C15–16 hydrocarbon fractions. To take an example, the C11–C12 hydrocarbon fraction will tend to comprise a mixture of paraffins and olefins having from 11–12 carbon atoms, in addition to alcohols having from 9–10 carbon atoms. However, the C11–C12 hydrocarbon fraction may additionally comprise paraffins, olefins and alcohols of higher or lower carbon number, depending on the boiling point range of the fraction.

For detergent applications, a preferred hydrocarbon fraction is a C11–C14 hydrocarbon fraction.

These hydrocarbon fractions can be used individually as feed to alkoxylation step (c), but two or more of these fractions may also be combined into a feed stream to the alkoxylation step (c). The process of the present invention is particularly suitable when using C11–C12 hydrocarbon streams and C13–C14 hydrocarbon streams as feed in step (c).

In a preferred embodiment the hydrocarbon fraction recovered after fractional distillation in step (b) comprises at least about 2%, preferably at least about 10%, more preferably at least about 30% by weight of alcohols.

The alkoxylation step is carried out by reaction of the at least one hydrocarbon fraction obtained from step (b) with an alkylene oxide in the presence of an alkoxylation catalyst. The alcohols present in the hydrocarbon fraction obtained from step (b) react with the alkylene oxide to produce an alkoxylated alcohol composition comprising one or more alkoxylated alcohols.

The alkylene oxide reactant can be any alkylene oxide suitable for producing alkoxylated alcohols and is preferably selected from ethylene oxide, propylene oxide, butylene oxide, and mixtures thereof, more preferably ethylene oxide, propylene oxide and mixtures thereof and especially ethylene oxide.

Any alkoxylation catalyst is suitable for use herein. Both acidic and basic alkoxylation catalysts can be used. Conventional alkoxylation catalysts include the basic salts and hydroxides of the alkali metals of Group I of the Periodic Table, e.g., sodium, potassium, rubidium, and cesium, and the basic salts and hydroxides of certain of the alkaline earth metals of Group II of the Periodic Table, e.g., calcium, strontium, barium and in some cases magnesium. Conventional acidic alkoxylation catalysts include, broadly, the Lewis acid or Friedel-Crafts catalysts. Specific examples of these acid catalysts are the fluorides, chlorides, and bromides of boron, antimony, tungsten, iron, nickel, zinc, tin, aluminum, titanium and molybdenum.

Another class of alkoxylation catalysts suitable for use herein are those based on rare-earth metals. EP-A-345861, U.S. Pat. No. 5,057,627 and WO02/047817 describe alkoxylation processes catalyzed by phosphate salts of the rare earth elements. These catalysts are typically prepared by adding an aqueous solution of a rare earth compound such as lanthanum chloride to an aqueous sodium orthophosphate or $H_3PO_4$ solution.

A further class of alkoxylation catalysts suitable for use herein include the double metal cyanide (DMC) catalysts. Conventional DMC catalysts are prepared by reacting aqueous solutions of metal salts and metal cyanide salts to form a precipitate of the DMC compound. Suitable DMC catalysts include those disclosed in EP-A-1276562.

Especially preferred alkoxylation catalysts for use herein are hydroxides of the alkali metals of Group I of the Periodic Table, for example, potassium hydroxide and sodium hydroxide.

Preferred alkoxylated alcohol compositions which are prepared by the present process are those which comprise one or more alkoxylated alcohols having the formula (IV):

$$R^1\text{—O-}(EO)_p\text{-}(PO)_q\text{-}(BO)_r\text{—H} \qquad (IV)$$

wherein $R^1$ is a straight chain or branched alkyl group having from 1 to 30 carbon atoms, EO, PO and BO represent ethyleneoxy, propyleneoxy and butyleneoxy moieties, and p, q and r are integers of from 0 to 70. Alkoxylated alcohols which are especially suitable for the purpose of detergent applications are compounds of formula (IV) wherein $R^1$ is an alkyl group having from 6 to 22 carbon atoms, preferably from 9 to 15 carbon atoms, p is in the range of from x to y, q is zero and r is zero.

In formula (IV) the EO, PO and BO groups can be distributed randomly along the alkoxide chain or be present as block (co)-polymers.

In the case of basic alkoxylation catalysts such as KOH, it is preferred to neutralize the KOH after the alkoxylation step (c) and before step (d). This can be done by addition of an appropriate acid, e.g. acetic acid.

Step (d) of the present process involves recovery of the alkoxylated alcohol composition from the reaction product of alkoxylation step (c). This can be achieved by methods known in the art. In particular, the unreacted paraffins and olefins can be evaporated off by any distillation method known in the art.

The invention will now be illustrated by the following example without limiting the scope of the invention to this particular embodiment.

EXAMPLE 1

Ethoxylation of a C13/14 Distillation Fraction of a Fischer-Tropsch Reaction Product Stream Approximately 1405 g of a C13/14 distillation fraction removed from the product stream of a Fischer-Tropsch hydrocarbon synthesis reaction using a Co/Ti catalyst and having the composition as given in Table 1, was charged to a dry, nitrogen flushed, stainless steel reactor. A nominal molecular weight of 172 g/mol was calculated for the alcohols in the C13/14 distillation fraction, and an average EO number of final ethoxylate was targeted to 6.5. A 50% aqueous KOH solution was added to catalyze the reaction, at a level of 0.1% w on total product. The reaction mixture was stirred at 500 rpm, and temperature was adjusted to 130° C. The pressure in the reactor was adjusted with nitrogen to 2 Bara, and 40 g ethylene oxide was added to the reactor in about 2.5 hours. Pressure in the reactor was monitored carefully. During addition of the ethylene oxide the pressure increased to 2.6 Bara, and dropped slowly to 0.72 Bara, indicating that the ethylene oxide was reacting with the reaction mixture.

TABLE 1

Composition of C13/14 distillation fraction from a Fischer-Tropsch reaction product stream

| Component | % m/m |
|---|---|
| Alcohols | |
| C10 | 0.14 |
| C11 | 3.17 |
| C12 | 1.35 |
| C13 | <0.01 |
| Alkanes | |
| n-C10 | <0.01 |
| n-C11 | <0.01 |
| n-C12 | 0.7 |
| n-C13 | 42.9 |
| n-C14 | 29.3 |
| n-C15 | <0.01 |
| Olefins | |
| α- C13 | 7.13 |
| β- C13 | 3.23 |
| α- C14 | 7.25 |
| β- C14 | 1.50 |
| Others C13 + C14 | 1.21 |
| Total* | 97.9* |

*other components in low concentration are branched paraffins - and branched olefin isomers After reacting down for two hours to constant pressure, the reaction mixture was cooled down to 80° C. Subsequently 1.7 g, 99.8% w acetic acid was added, while stirring at 500 rpm, to neutralize the reaction mixture. No further purification was done. Total weight of product recovered was 1533.1 g.

After neutralization, the ethoxylated product stream was subjected to distillation, to remove un-reacted components, i.e., paraffins, and olefins. Distillation took place at 10 mm Hg pressure using a 15 tray Fischer packed distillation column, and reboiler temperature was allowed to increase to 250° C. maximum.

The resulting bottom product (approximately 150 g) was subjected to $^{13}C$ NMR analysis to determine product composition and structure of the ethoxylate.

Results indicated mainly the presence of ethoxylated alcohols with 9 to 10 ethylene oxide units. Other constituents present in minor amounts were non-reacted alcohols and polyethylene glycols. Formation of the latter is caused by reaction with water diluent of the KOH solution.

We claim:

1. A process for the preparation of an alkoxylated alcohol composition comprising one or more alkoxylated alcohols wherein the process comprises the steps of:
   (a) reacting carbon monoxide with hydrogen under Fischer-Tropsch reaction conditions in the presence of a Fischer-Tropsch catalyst;
   (b) separating from the product of step (a) at least one hydrocarbon fraction comprising paraffins having from 9 to 17 carbon atoms and olefins having from 9 to 17 carbon atoms, the hydrocarbon fraction additionally comprising at least a portion of alcohols;
   (c) contacting one or more of the hydrocarbon fractions obtained in step (b) with an alkylene oxide; and
   (d) recovering an alkoxylated alcohol composition from the reaction product of step (c).

2. The process of claim 1 wherein the Fischer-Tropsch catalyst comprises cobalt or iron.

3. The process of claim 2 wherein the Fischer-Tropsch catalyst comprises cobalt and wherein the pressure in step (a) is from about 50 to about 150 bar and the temperature is from about 150 to about 250° C.

4. The process of claim 1 wherein the Fischer-Tropsch catalyst is a supported cobalt catalyst wherein the support is selected from the group consisting of titania, zirconia, silica, and mixtures thereof.

5. The process of claim 1 wherein the Fischer-Tropsch catalyst is a cobalt catalyst on a titania support.

6. The process of claim 1 wherein the Fischer-Tropsch catalyst is an iron-based catalyst.

7. The process of claim 1 wherein step (a) comprises reacting carbon monoxide with hydrogen at a temperature in the range of from about 125 to about 350° C. and a pressure in the range from about 5 to about 150 bar abs.

8. The process of claim 1 wherein the catalyst and process conditions in step (a) are selected such that the product obtained in step (a) comprises in the range from about 2 to about 20 percent by weight of a C11 to C14 hydrocarbon fraction which comprises at least about 2 percent by weight of C9 to C12 mono-alcohols.

9. The process of claim 8 wherein step (a) is carried out using a cobalt-based Fischer-Tropsch catalyst based on cobalt and titania at a temperature of from about 175 to about 275° C. and a pressure of from about 30 to about 65 bar abs.

10. The process of claim 8 wherein step (a) is carried out using an iron-based Fischer-Tropsch catalyst.

11. The process of claim 1 wherein the alkoxylated alcohols have the formula (IV):

$$R^1\text{—O-(EO)}_p\text{-(PO)}_q\text{-(BO)}_r\text{-H} \qquad (IV)$$

wherein $R^1$ is a straight chain or branched alkyl group having from 1 to 30 carbon atoms, EO, PO and BO represent ethyleneoxy, propyleneoxy and butyleneoxy moieties, and p, q and r are integers of from 0 to 70.

12. The process of claim 11 wherein p is 1 or 2, q is zero and r is zero.

13. The process of claim 1 wherein the hydrocarbon fraction that is fed to step (c) is a C13/C14 hydrocarbon fraction.

14. The process of claim 1 wherein the hydrocarbon fraction that is fed to step (c) is a C11/C12 hydrocarbon fraction.

15. The process of claim 1 wherein step (a) is carried out using a reaction regime selected from a group consisting of a fixed bed regime, a slurry phase regime, and an ebullating fed regime.

16. The process of claim 15 wherein a fixed bed regime is used and the gas hourly space velocity is in the range of from about 500 to about 2500 N1/1/h.

17. The process of claim 15 wherein a slurry phase regime is used and the gas hourly space velocity is in the range from about 1500 to about 7500 N1/1/h.

* * * * *